(12) United States Patent
Dwivedi et al.

(10) Patent No.: US 9,611,225 B2
(45) Date of Patent: Apr. 4, 2017

(54) PROCESS FOR PREPARATION OF ANDROGEN RECEPTOR ANTAGONIST

(71) Applicant: Cadila Healthcare Limited, Ahmedabad (IN)

(72) Inventors: Shri Prakash Dhar Dwivedi, Ahmedabad (IN); Kumar Kamlesh Singh, Ahmedabad (IN); Ganpat Dan Shimbhu Charan, Ahmedabad (IN)

(73) Assignee: Cadila Healthcare Limited, Ahmedabad Gujarat (IN)

( * ) Notice: Subject to any disclaimer, the term of this patent is extended or adjusted under 35 U.S.C. 154(b) by 152 days.

(21) Appl. No.: 14/606,390

(22) Filed: Jan. 27, 2015

(65) Prior Publication Data

US 2015/0210649 A1    Jul. 30, 2015

(30) Foreign Application Priority Data

Jan. 27, 2014  (IN) .......................... 292/MUM/2014
Jun. 4, 2014    (IN) ......................... 1845/MUM/2014

(51) Int. Cl.
*C07D 233/86*    (2006.01)
*C07C 231/12*    (2006.01)

(52) U.S. Cl.
CPC .......... *C07D 233/86* (2013.01); *C07C 231/12* (2013.01)

(58) Field of Classification Search
None
See application file for complete search history.

(56) References Cited

U.S. PATENT DOCUMENTS

2013/0190507 A1*  7/2013  Jain ...................... C07D 235/02
                                                              548/301.4

* cited by examiner

*Primary Examiner* — Matthew Coughlin
*Assistant Examiner* — Po-Chih Chen
(74) *Attorney, Agent, or Firm* — Schwegman Lundberg & Woessner, P.A.

(57) ABSTRACT

The present invention provides an isopropanol solvate of enzalutamide. The present invention also provides a process for the preparation of androgen receptor antagonist. In particular, the present invention provides a process for the preparation of enzalutamide or its pharmaceutically acceptable salts, hydrates, solvates, polymorphs or intermediates thereof.

6 Claims, 5 Drawing Sheets

PROCESS FOR PREPARATION OF ANDROGEN RECEPTOR ANTAGONIST

CLAIM OF PRIORITY

This application claims the benefit of priority under 35 U.S.C. §119 to Indian Provisional Patent Application No. 1845/MUM/2014, filed on Jun. 4, 2014, and to Indian Provisional Patent Application No. 292/MUM/2014, filed on Jan. 27, 2014, each of which is incorporated by reference herein in its entirety.

FIELD OF THE INVENTION

The present invention relates to a process for preparation of androgen receptor antagonist. In particular, the invention relates to a process for preparation of enzalutamide or its pharmaceutically acceptable salts, hydrates, solvates, polymorphs or intermediates thereof.

BACKGROUND OF THE INVENTION

The following discussion of the prior art is intended to present the invention in an appropriate technical context and allow its significance to be properly appreciated. Unless clearly indicated to the contrary, however, reference to any prior art in this specification should be construed as an admission that such art is widely known or forms part of common general knowledge in the field.

4-(3-(4-cyano-3-(trifluoromethyl)phenyl)-5,5-dimethyl-4-oxo-2-thioxoimidazolidin-1-yl)-2-fluoro-N-methylbenzamide (INN name is Enzalutamide; CAS No. [915087-33-1] is an androgen receptor inhibitor for the treatment of castration-resistant prostate cancer, having molecular weight 464.44 g/mol and molecular formula $C_{21}H_{16}F_4N_4O_2S$, and can be structurally represented as Formula (I).

U.S. Pat. No. 7,709,517 B2 (the U.S. '517 patent) discloses diarylhydantoin compounds, including diarylthiohydantoins, and methods for synthesizing them and using them for the treatment of hormone refractory prostate cancer. Example 56 of the U.S. '517 patent discloses the process for preparation of enzalutamide.

U.S. PG-Pub. No. 2013/190507 A1 (the U.S. '507 A1) discloses process for the preparation of diarylthiohydantoin and diarylhydantoin compounds including enzalutamide. Example-5 of the U.S. '507 A1 discloses enzalutamide as compound of Formula I-1 in 82% yield as white powder with 0.14% moisture by KF and having greater than 99.9% purity by HPLC. Further, example-8 of the U.S. '507 A1 discloses enzalutamide as compound of Formula I-1 obtained by purifying crude material by column chromatography wherein the analytical data were in agreement with that of example-5.

The U.S. '507 A1 discloses process for the preparation of enzalutamide and related compounds. The U.S. '507 A1 discloses the preparation of enzalutamide designated as compound I, 2-I starting from compound A as depicted in scheme-1.

(I)

Scheme-1

$R^1 = \text{---}L^1\text{---}C(\text{=}O)NH_2, \text{---}L^1\text{---}C(\text{=}O)NHR^4,$
$\text{---}L^1\text{---}C(\text{=}O)NR^4R^5, \text{---}L^1\text{---}CN$

The U.S. '507 A1 also discloses the alternative synthesis of compounds of I or 2-Ia, wherein $R^7$ is —C(=O)OH which is illustrated in scheme-2 below.

Scheme-2

The U.S. '507 A1 in example-10 further discloses the process for the preparation of diarylhydantoin of formula M-1 by reacting 4-(1-Carboxy-1-methyl)-ethylamino)-2-flouro-benzoic acid and 4-isothiocyanato-2-triflouromethylethylbenzonitrile in presence of triethylamine in ethanol solvent as depicted in scheme-3.

Scheme-3

U.S. PG-Pub. No. 2013/0079372 A1 discloses the process for the preparation of substituted phenylcarbamoyl alkylamino arene compounds and N,N'-bis-arylurea compounds. These compounds are intermediate compounds for the preparation of diarylhydantoin compounds as disclosed below.

International (PCT) Publication No. WO 2014/043208 A1 discloses a pharmaceutical composition comprising a solid dispersion containing enzalutamide and a polymer, wherein the polymer is 0.5 to 7 parts by weight, with respect to 1 part by weight of the enzalutamide.

International (PCT) Publication No. WO 2014/041487 A2 discloses process for the preparation of cyrstalline Form R1 of enzalutamide. Also discloses crystalline form R2 and an amorphous form of enzalutamide and their process for preparation.

Therefore, there is need to provide an alternative process for the preparation of androgen receptor inhibitors like enzalutamide.

SUMMARY OF THE INVENTION

In one general aspect, there is provided an enzalutamide solvate.

In another general aspect, there is provided a substantially pure enzalutamide.

In another general aspect, there is provided a process for the preparation of enzalutamide of Formula (I), the process comprising:
reacting a compound of Formula (VI)

with a compound of Formula (V)

wherein L is Cl, Br, I or a leaving group,
to obtain a compound of Formula (IV)

optionally, purifying the compound of Formula (IV);
reacting the compound of Formula (IV) with a compound of Formula (II)

to obtain the enzalutamide of Formula (I); and
optionally, purifying the enzalutamide of Formula (I) in one or more of solvents.

In another general aspect, there is provided a process for the preparation of compound Formula (IV)

the process comprising:
reacting a compound of Formula (VI)

with a compound of Formula (V)

wherein L is Cl, Br, I or a leaving group,
to obtain the compound of Formula (IV); and
optionally, purifying the compound of Formula (IV).

In another general aspect, there is provided an enzalutamide substantially free from one or more of impurities when measured by area percentage of HPLC.

In another general aspect, there is provided a pharmaceutical composition comprising substantially pure enzalutamide together with one or more of pharmaceutically acceptable carriers, excipients and diluents.

In another general aspect, there is provided a pharmaceutical composition comprising enzalutamide substantially free from one or more of impurities together with one or more of pharmaceutically acceptable carriers, excipients and diluents.

DETAILED DESCRIPTION OF THE INVENTION

All ranges recited herein include the endpoints, including those that recite a range "between" two values. Terms such as "about", "generally", and "substantially," are to be construed as modifying a term or value such that it is not an absolute. This includes, at very least, the degree of expected experimental error, technique error and instrument error for a given technique used to measure a value.

The terms such as "treating", "reacting", and "condensing" have meanings as widely used by general prior art in the field of invention and can be easily understood by those skilled in the art.

Optionally, the solution, prior to any solids formation, can be filtered to remove any undissolved solid and/or solid impurities prior to removal of the solvent. Any filtration system and filtration techniques known in the art can be used.

The term "substantially pure" herein means enzalutamide having a purity of at least about 98% by area percentage of HPLC. In particular, enzalutamide having a purity of at least about 99%, more particularly, a purity of at least about 99.5%, further more particularly, a purity of at least about 99.8%, most particularly, a purity of at least about 99.9% by area percentage of HPLC.

The term "substantially free" herein means enzalutamide having impurity-A, impurity-B, impurity-C, impurity-D, impurity-E and impurity-F less than about 0.15% by area percentage of HPLC. In particular, less than about 0.10% by area percentage of HPLC. More particular, the impurity-C, impurity-D, impurity-E and impurity-F not in detectable amount by area percentage of HPLC.

The terms used throughout the description is defined herein below.

"TEA" refers to triethylamine.
"TBA" refers to tert-butyl amine.
"DIPA" refers to diisopropyl amine.
"DIPEA" refers to diisopropyl ethylamine.
"DBU" refers to 1,8-diazabicyclo[5.4.0]undec-7-ene.
"DABCO" refers to 1,4-diazabicyclo[2.2.2]octane.
"DBN" refers to 1,5-Diazabicyclo[4.3.0]non-5-ene
"HPLC" refers to high performance liquid chromatography.

In one general aspect, there is provided a solvate of enzalutamide solvate.

In general, the enzalutamide solvate is isopropanol solvate characterized by X-ray powder diffraction (XRD) having characteristic peaks expressed in degrees 2θ (±0.2° 2θ) at about 4.4°, 8.9°, 13.5°, 14.7°, and 23.2±0.2° 2θ. The enzalutamide isopropanol solvate is further characterized by X-ray powder diffraction having characteristic peaks expressed in degrees 2θ (±0.2° 2θ) at about 4.4°, 7.3°, 8.9°, 10.6°, 13.5°, 14.7°, 16.1°, 18.0°, 18.9°, 20.7°, 23.2°, 25.5°, and 27.1±0.2°.

In general, the enzalutamide isopropanol solvate is characterized by differential scanning calorimetry (DSC) having first onset at about 117±5° C. and endothermic peak at about 123±5° C. and second onset at about 196±5° C. and endothermic peak at about 198±5° C.

In general, the enzalutamide isopropanol solvate is characterized by thermogravimetric analysis (TGA) having weight loss of about 5.3%.

In general, the enzalutamide isopropanol solvate is containing isopropanol of at least about 5.2% wt/wt to about 6.5% wt/wt.

Figure 3:
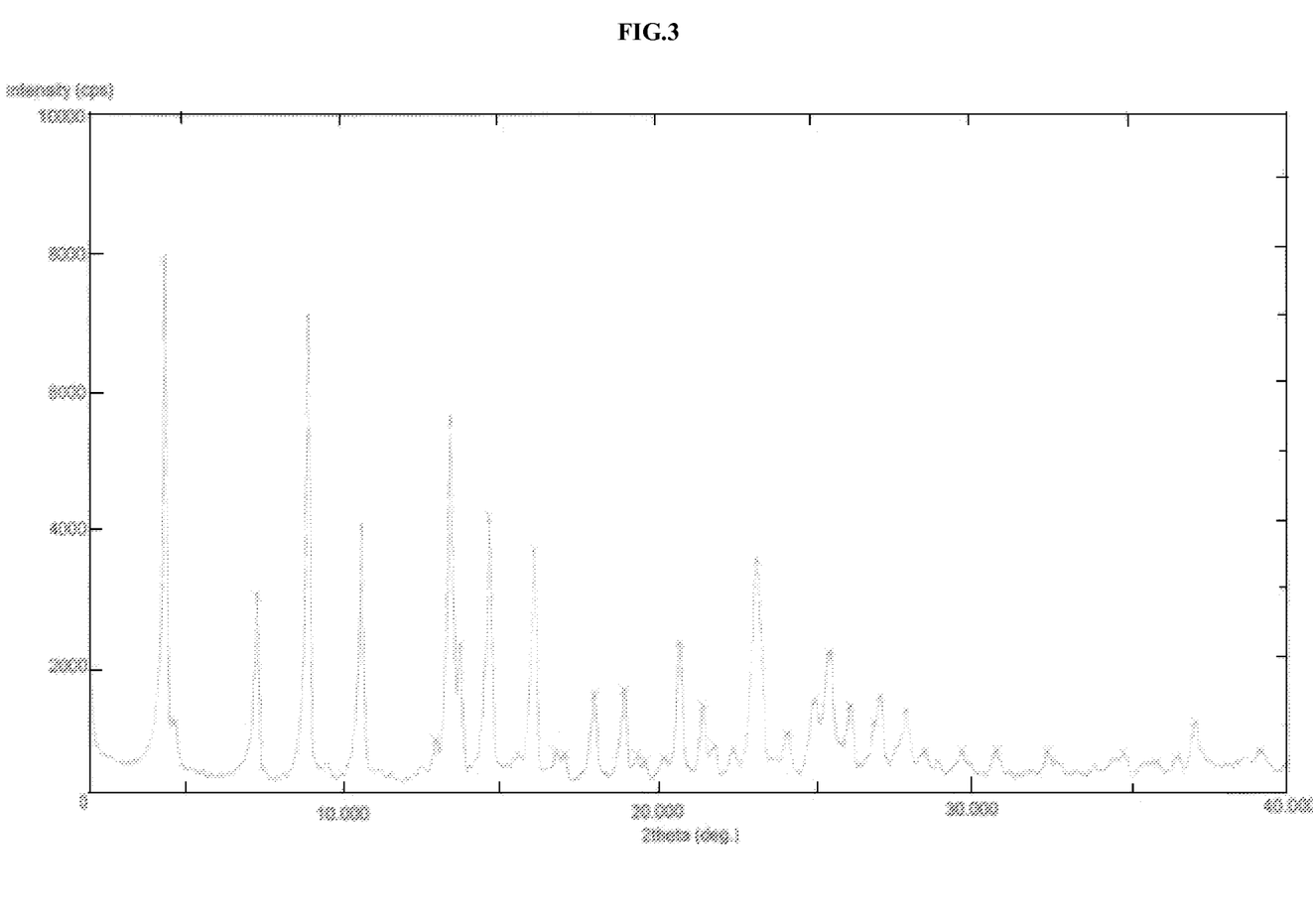
FIG. 3: X-ray powder diffraction pattern of crystalline enzalutamide isopropanol solvate.
Figure 4:
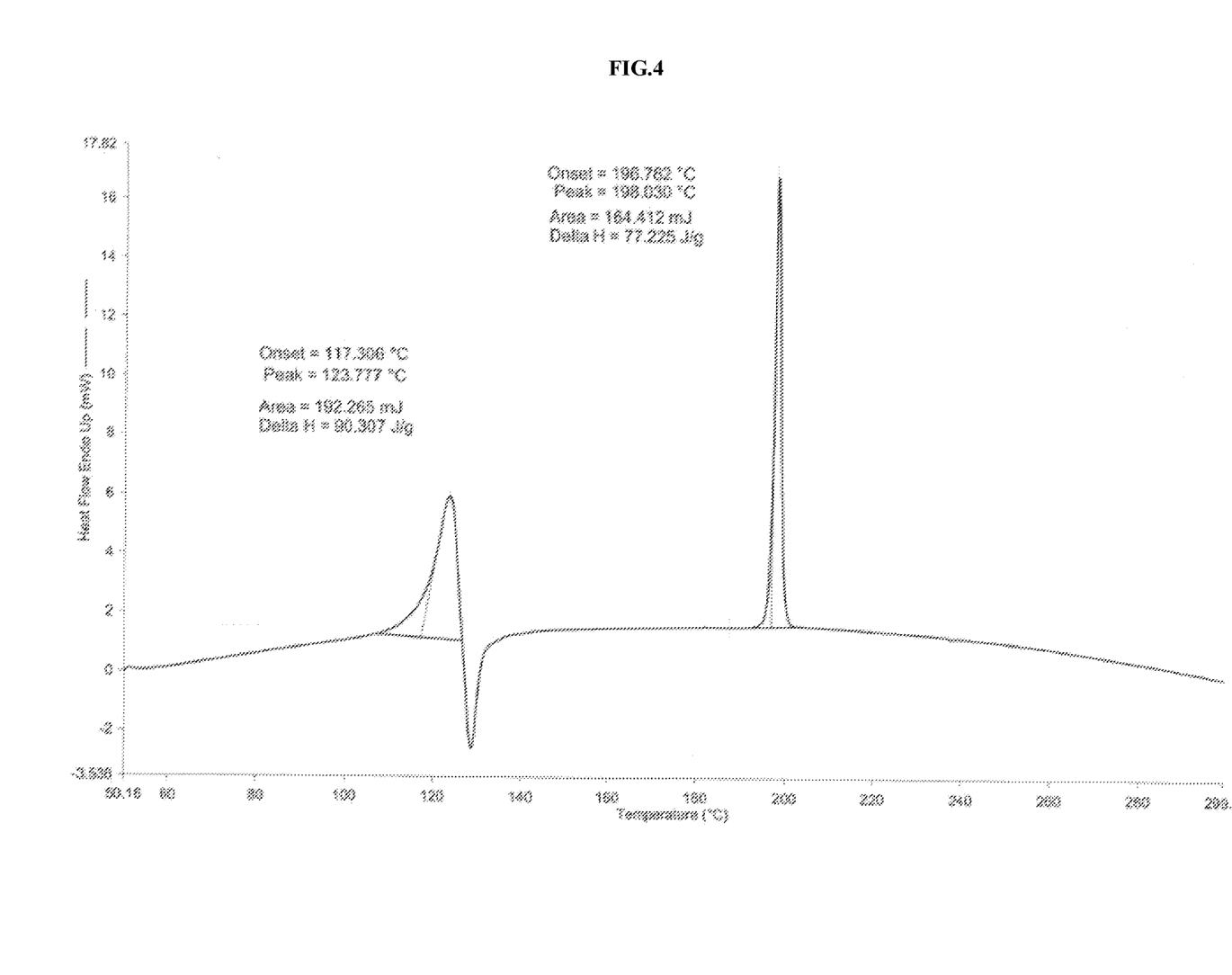
FIG. 4: Differential Scanning calorimetry (DSC) of crystalline enzalutamide isopropanol solvate.
Figure 5:
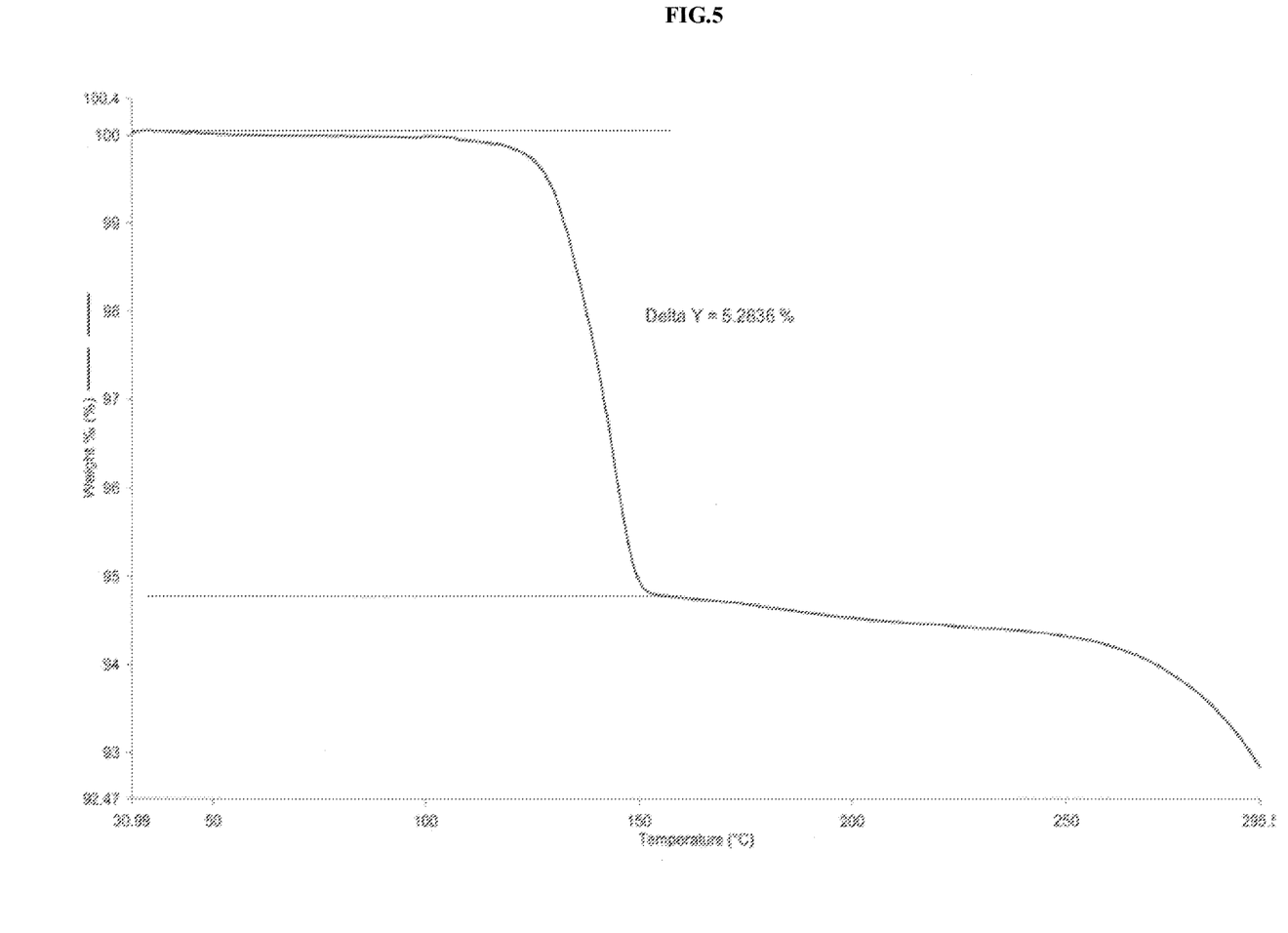
FIG. 5: Thermogravimetric analysis (TGA) of crystalline enzalutamide isopropanol solvate.

In another general aspect, the enzalutamide isopropanol solvate is characterized by the x-ray powder diffraction pattern substantially the same as that shown in FIG. 3, the differential scanning calorimetry substantially the same as that shown in FIG. 4 and the thermogravimetry analysis substantially the same as that shown in FIG. 5.

In another general aspect, there is provided a substantially pure enzalutamide.

In general, the impurities of enzalutamide may be one or more of impurity-A to impurity-E represented by structural formula as herein below:

(Diketo-Impurity-A)

(Desfluoro-Impurity-B)

(Impurity-C)

(Impurity-D)

(Impurity-E)

(Impurity-F)

In another general aspect, there is provided a process for the preparation of enzalutamide of Formula (I)

(I)

the process comprising:
reacting a compound of Formula (VI)

(VI)

with a compound of Formula (V)

(V)

wherein L is Cl, Br, I or a leaving group,
to obtain a compound of Formula (IV)

(IV)

optionally, purifying the compound of Formula (IV);
reacting the compound of Formula (IV) with a compound of Formula (II)

(II)

to obtain the enzalutamide of Formula (I); and
optionally, purifying the enzalutamide of Formula (I) in one or more of solvents.

In general, the compound enzalutamide of Formula (I) may be prepared by reacting the compound of Formula (IV) with the compound of Formula (II) optionally in presence of a base in one or more solvents.

The base comprises of inorganic or organic base. The inorganic base comprises one or more of sodium hydroxide, potassium hydroxide, lithium hydroxide; sodium carbonate, potassium carbonate, sodium bicarbonate, potassium bicarbonate; and ammonia or its aqueous solution; or the organic base comprises one or more of methyl amine, ethyl amine, TEA, TBA, DIPA, DIPEA, pyridine, piperidine, morpholine, DBU, DABCO and DBN. In particular, TEA may be used.

In solvents comprises one or more of esters selected from ethyl acetate, isopropyl acetate, t-butyl acetate, and isobutyl acetate; hydrocarbons selected from toluene, xylene, ethyl benzene, heptane, hexane, and cyclohexane; chlorinated solvents selected from methylene dichloride, ethylene dichloride, chlorobenzene, chloroform, and carbon tetrachloride. In particular, toluene, xylene, methylene dichloride, and ethyl acetate may be used.

The prior art U.S. '507 A1 discloses the coupling of compound A and compound B in the presence of a catalytic amount of both a copper (I) catalyst and a beta-dione ligand such as 2-acetylcyclohexanone, in a polar solvent and with heating to a temperature of about 90-120° C. The work-up involves addition of water to the cooled reaction mixture followed by washing with water-immiscible organic solvent such as isopropyl acetate. The aqueous layer is acidified to isolate compound C herein compound (IV) by precipitation, filtration and drying.

The present invention has advantages over the prior art. The process is simple and doesn't involve use of any catalyst. The work-up is also very simple to isolate compound (IV).

The prior art U.S. '507 A1 further discloses reacting compound C herein compound (IV) with alkylating agent like methyl iodide to obtain ester of Formula D. The reaction is performed in presence of potassium carbonate as base with varying molar equivalents.

The present invention has advantage over the prior art. The process herein doesn't require conversion of compound (IV) to its ester or any other derivative before reacting with compound of Formula (II).

In general, the reaction of compound (VI) and compound (II) may be done at temperature ranging from 25° C. to boiling point of solvent. In particular, the reaction may be performed at 25° C. to 150° C. Alternatively, the reaction may also be performed under cooled conditions having temperature from −25° C. to about 25° C. In particular, from −10° C. to about 10° C.

In general, the purification of compound (IV) is performed in one or more of solvents. The solvents comprises one or more of alcohols selected from methanol, ethanol, isopropanol, butanol, t-butanol, and isoamylalcohol; ketones selected from acetone, methyl isobutyl ketone, and methyl ethyl ketone; esters selected from ethyl acetate, isopropyl acetate, t-butyl acetate, and isobutyl acetate; chlorinated solvents selected from methylene dichloride, ethylene dichloride, and chlorobenzene. In particular, methanol, acetone, ethyl acetate, methylene dichloride may be used.

The embodiments of the invention further comprises reacting the compound of Formula (IV) with the compound of Formula (II) optionally in presence of a base in one or more solvents to obtain enzalutamide of Formula (I).

In general, the base comprises of inorganic or organic base. The inorganic base comprises one or more of sodium hydroxide, potassium hydroxide, lithium hydroxide; sodium carbonate, potassium carbonate, sodium bicarbonate, potassium bicarbonate, and ammonia or its aqueous solution; or the organic base comprises one or more of methyl amine, ethyl amine, TEA, TBA, DIPA, DIPEA, pyridine, piperidine, morpholine, DBU, DABCO and DBN. In particular, TEA may be used.

In general, the solvents comprises one or more of alcohols selected from methanol, ethanol, isopropanol, butanol, t-butanol, and isoamylalcohol; esters selected from ethyl acetate, isopropyl acetate, t-butyl acetate, and isobutyl acetate; hydrocarbons selected from toluene, xylene, ethyl benzene, heptane, hexane, and cyclohexane; chlorinated solvents selected from methylene dichloride, ethylene dichloride, chlorobenzene, chloroform, and carbontetrachloride. In particular, toluene, xylene, methylene dichloride, and ethyl acetate may be used.

In general, it is observed that the reaction of the compound (IV) with the compound (II) results in the formation of impurity-A to the level of 0.3 to 0.5%, when measured by area percentage of HPLC due to the presence of phosgene in thiophosgene during preparation of compound (II). Also, enzalutamide has the tendency to get oxidized to form the impurity-A in presence of oxygen.

The process disclosed in prior art U.S. '507 A1 results in the formation of impurity-A to the level of 0.3 to 0.5% when measured by area percentage of HPLC.

Therefore, the present invention provides the preparation of enzalutamide wherein the reaction of the compound (IV) and the compound (II) is done in presence of phenol. The phenol arrest the formation of impurity-A during the reaction and thereby provide enzalutamide substantially free from impurity-A.

In another general aspect, there is provided a process for the preparation of enzalutamide of Formula (I) substantially free from impurity-A (I)

(Impurity-A)

the process comprising:
reacting a compound of Formula (IV)

(IV)

with a compound of Formula (II)

(II)

optionally in presence of phenol to obtain the enzalutamide of Formula (I) substantially free from diketo-impurity-A.

In another general aspect, there is provided an enzalutamide of Formula (I) substantially free from diketo-impurity-A.

In general, the starting compound (VI) is the potential source for the formation of desflouro-impurity-B. The presence of higher amount of desfluoro analouge of the compound (VI) results in 0.2 to 0.3% of impurity-B, when measured by area percentage of HPLC.

The use of starting material compound (VI) containing desfluoro analogue of about 0.15% or less, results in enzalutamide containing desfluoro-impurity-B of about 0.15% or less by area percentage of HPLC.

In general, the starting material compound (VI) containing desfluoro analogue of about 0.15% or less, in particular containing 0.10% or less, more particular, containing 0.05% or less, most particularly containing not in detectable amount may be used to obtain enzalutamide substantially free from desfluoro-impurity-B.

In another general aspect, there is provided an enzalutamide of Formula (I) substantially free from desflouro-impurity-B.

The compound (I) enzalutamide may be isolated by usual work-up wherein the solvent after completion of the reaction may be removed by filtration or evaporation. Alternatively, the solvent may be distilled to obtain residue which may be extracted with one or more solvents selected from dimethylformamide, dimethylacetamide, dimethylsulfoxide, N-methyl pyrrolidone, tetrahydrofuran, acetonitrile, ethylacetate, toluene, and xylene. The reaction mixture may be acidified with an acid selected from hydrochloric acid, sulfuric acid, acetic acid, or formic acid, thereby to adjust the acidic pH.

In general, the purification of enzalutamide is done in one or more of solvents. The organic solvents comprises one or more of alcohols selected from methanol, ethanol, isopropanol, butanol, t-butanol, and isoamylalcohol; ketones selected from acetone, methyl isobutyl ketone, and methyl ethyl ketone; esters selected from ethyl acetate, isopropyl acetate, t-butyl acetate, and isobutyl acetate; chlorinated solvents selected from methylene dichloride, ethylene dichloride, and chlorobenzene. In particular, methanol, acetone, ethyl acetate, methylene dichloride may be used.

In another general aspect, there is provided crystalline Form-A of enzalutamide characterized by an x-ray powder diffraction (XRD) having characteristic peaks expressed in degrees 2θ (±0.2° 2θ) at about 13.1°, 13.4°, 14.3°, 16.6°, 21.1°, 22.7° and 24.4°±0.2° 2θ. The crystalline Form-A of enzalutamide is further characterized by X-ray powder diffraction having characteristic peaks expressed in degrees 2θ (±0.2° 2θ) at about 9.7°, 12.2°, 13.1°, 13.4°, 14.3°, 14.9°, 16.6°, 18.8°, 19.5°, 21.1°, 21.7°, 22.7°, 24.4°, 25.4°, 26.4°, 27.9°, 28.9° and 30.8°±0.2° 2θ.

Figure 1:
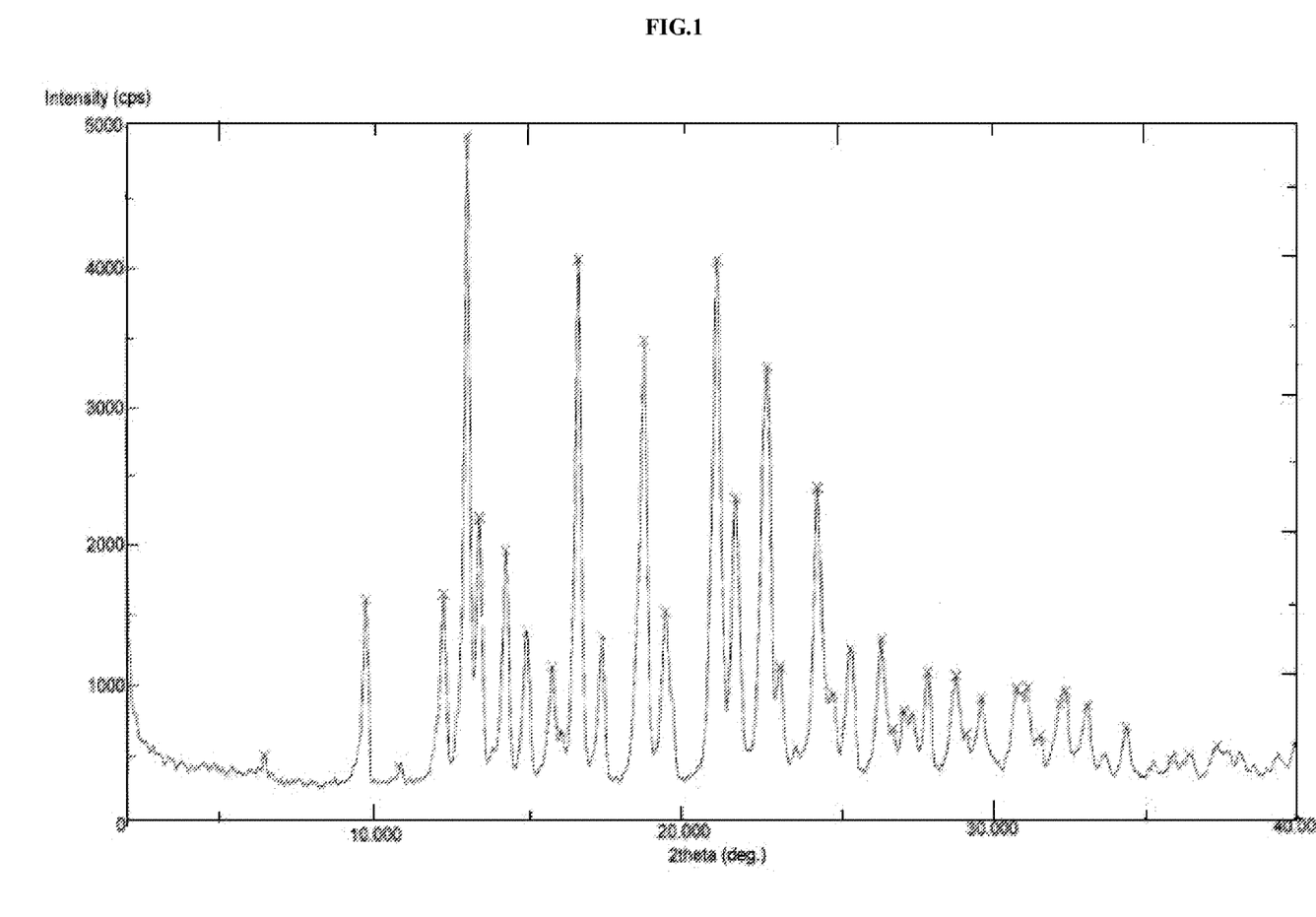
FIG. 1: X-ray powder diffraction pattern of enzalutamide crystalline Form-A.

In another general aspect, there is provided crystalline Form-A of enzalutamide characterized by X-ray powder diffraction pattern substantially the same as that shown in FIG. 1.

In general, the crystalline enzalutamide Form-A is further characterized by differential scanning calorimetry (DSC) having onset at about 197±5° C. and an endothermic peak at about 198±5° C.

Figure 2:
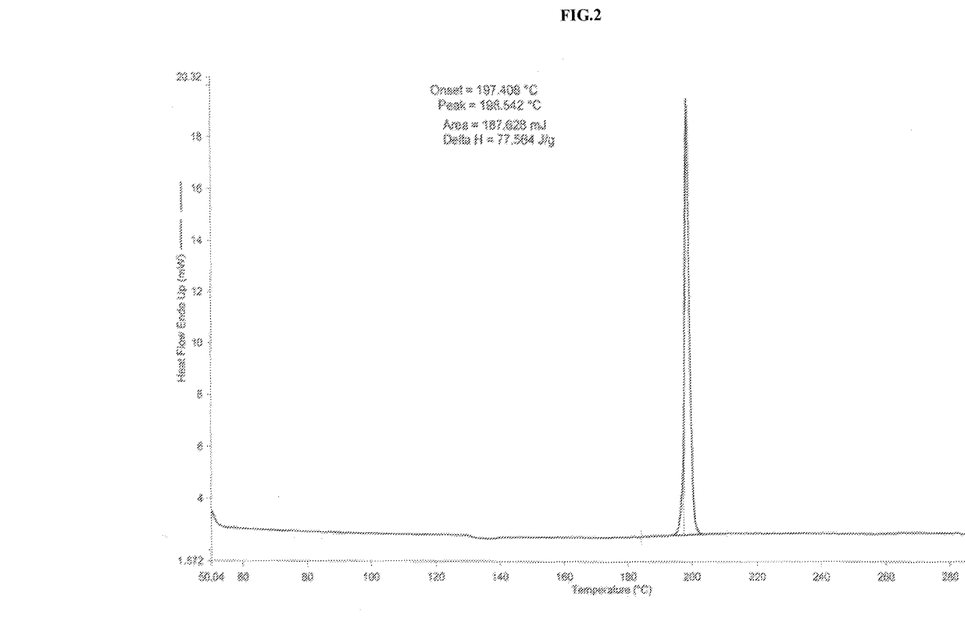
FIG. 2: Differential Scanning calorimetry of crystalline enzalutamide Form-A.

In another general aspect, there is provided crystalline Form-A of enzalutamide characterized by differential scanning calorimetery substantially the same as that shown in FIG. 2.

In another general aspect, there is provided a process for the preparation of compound of Formula (IV)

(IV)

the process comprising:
reacting a compound of Formula (VI)

(VI)

with a compound of Formula (V)

(V)

wherein L is Cl, Br, I or a leaving group,
to obtain the compound of Formula (IV); and
optionally, purifying the compound of Formula (IV).

The starting compound of Formula (II), wherein L is bromine may be prepared by the process disclosed in the prior art for example *Tetrahedron Letters,* 1998 vol. 39 (52) p. 9621-9622 or *Journal of the American Chemical Society,* 1949 vol. 71, p. 2234-2237 or *Journal of the Indian Chemical Society,* 1933 vol. 10, p. 592, which is incorporated herein as reference.

The starting compound of Formula (VI) may be prepared by the process disclosed in the prior art for example U.S. Pat. No. 7,709,517 B2 or U.S. 2012/0172406 A1 or *Journal of Medicinal Chemistry,* 2010 vol. 53(7) p. 2779-2796, which is incorporated herein as reference.

In general, the process for the preparation of enzalutamide may be in accordance with the reaction scheme-4 as depicted herein below.

Scheme-4

(IV)

In another general aspect, there is provided an enzalutamide of Formula (I) substantially free from one or more of impurities when measured by area percentage of HPLC.

In another general aspect, there is provided a pharmaceutical composition comprising substantially pure enzalutamide together with one or more of pharmaceutically acceptable carriers, excipients and diluents.

In another general aspect, there is provided a pharmaceutical composition comprising enzalutamide substantially free from one or more of impurities together with one or more of pharmaceutically acceptable carriers, excipients and diluents.

The present invention is further illustrated by the following example which is provided merely to be exemplary of the invention and do not limit the scope of the invention.

EXAMPLES

Example-1

Preparation of 2-((3-fluoro-4-(methylcarbamoyl) phenyl)amino)-2-methyl propanoic acid (IV)

In a 500 mL four necked round bottomed flask equipped with nitrogen atmosphere facility, mechanical stirrer, thermometer and an addition funnel, (10 g) 4-amino-2-fluoro-N-methylbenzamide, (16 g) bromo-isobutyric acid and 100 mL dichloromethane were added at room temperature. (25 mL) triethylamine was added and the reaction mixture was stirred for 15 hours at 20-30° C. After completion of reaction, the reaction mixture was concentrated completely UN at 40° C. 100 mL water was added and stirred for 1 hour. 7.5 mL hydrochloric acid was added and stirred for 30 min. The reaction mixture was cooled to 0-5° C. and stirred for 1 hour, filtered, washed with 25 mL water and dried to obtain 15.2 g titled compound with 94.97% purity by HPLC.

Example-2

Purification of 2-((3-fluoro-4-(methylcarbamoyl) phenyl)amino)-2-methyl propanoic acid (IV)

In a 500 mL four necked round bottomed flask equipped with nitrogen atmosphere facility, mechanical stirrer, thermometer and an addition funnel, (15 g) 2-((3-fluoro-4-(methylcarbamoyl)phenyl)amino)-2-methylpropanoic acid obtained in example-1 and 120 mL acetone were heated to 55 to 60° C. for 1 hour. The reaction mixture was cooled to 0 to 5° C. and the product thus obtained was filtered and dried under vacuum at 50° C. to obtain 12 g titled compound with 99.54% purity by HPLC.

Example-3

Preparation of 4-isothiocyanato-2-(trifluoromethyl)benzonitrile (II)

In a 500 mL four necked round bottomed flask equipped with nitrogen atmosphere facility, mechanical stirrer, thermometer and an addition funnel, (15 g) 4-amino-2-(trifluoromethyl)benzonitrile, 150 mL water and 75 mL dichloromethane were added at 20-30° C. The reaction mixture was stirred for 15 min and 9 mL thiophosgene was added. The reaction mixture was stirred for 4 hours. After completion of the reaction, the layers were separated and the organic layer was concentrated completely U/V at 40° C. 105 mL hexane was added to the concentrated reaction mass and cooled 0 to 5° C. The compound was filtered, washed with hexane and dried to obtain 20 g titled compound with 98% purity by HPLC.

Example-4

Preparation of Enzalutamide (I) in Absence of Phenol

In a 500 mL four necked round bottomed flask equipped with nitrogen atmosphere facility, mechanical stirrer, thermometer and an addition funnel (14 g) 4-isothiocyanato-2-(trifluoromethyl)benzonitrile and 150 mL chloroform were added. The reaction mixture was stirred for 15 min and 5 mL triethylamine was added at 20-30° C. The reaction mixture was heated to reflux for 15 min. (10 g) 2-((3-fluoro-4-(methylcarbamoyl)phenyl)amino)-2-methylpropanoic acid was added. The reaction mixture was refluxed for 6 hours. After the completion of the reaction, the reaction mixture was concentrated completely at 50° C. U/V. 20 mL isopropyl alcohol was added to the concentered reaction mass and stirred for 60 min at 20-30° C. The compound was filtered, washed with 2 mL of isopropyl alcohol and dried to obtain 76.92% yield of enzalutamide with 98.77% purity by HPLC. The diketo impurity-A is 0.87%.

Example-5

Preparation of Enzalutamide (I) in Presence of Phenol

In a 500 mL four necked round bottomed flask equipped with nitrogen atmosphere facility, mechanical stirrer, thermometer and an addition funnel (14 g) 4-isothiocyanato-2-(trifluoromethyl)benzonitrile and 150 mL chloroform were added. (10 g) phenol was added in to the reaction mixture. The reaction mixture was stirred for 15 min and 5 mL triethylamine was added at 20-30° C. The reaction mixture was heated to reflux for 15 min. (10 g) 2-((3-fluoro-4-(methylcarbamoyl)phenyl)amino)-2-methylpropanoic acid was added. The reaction mixture was refluxed for 6 hours. After the completion of the reaction, the reaction mixture was concentrated completely at 50° C. UN. 20 mL isopropyl alcohol was added to the concentered reaction mass and stirred for 60 min at 20-30° C. The compound was filtered, washed with 2 mL of isopropyl alcohol and dried to obtain 81.85% yield of enzalutamide as isopropanol solvate with 99.82% purity by HPLC. (Isopropanol content by GC: 5.92%). The diketo impurity-A is 0.06%.

Example-6

Purification of Enzalutamide (I)

In a 500 mL four necked round bottomed flask equipped with nitrogen atmosphere facility, mechanical stirrer, thermometer and an addition funnel (12 g) enzalutamide and (180 mL) isopropyl alcohol were added at 20-30° C. The reaction mixture was heated to reflux to obtain clear solution. (240 mg) activated Norit-A carbon. The reaction mixture was stirred for 15 to 30 min at 70-75° C. The reaction mixture was cooled to 20-30° C. and stirred for 1 hour. The enzalutamide was filtered, washed with 2 mL isopropyl alcohol and dried to obtain 10.45 g crystalline Form-A of enzalutamide with 99.85% purity by HPLC.

Impurity Profile:

Impurity-A: 0.05%; Impurity-B: 0.11%; Impurity-C: not detected; Impurity-D: not detected; Impurity-E: not detected and impurity-F: not detected.

While the present invention has been described in terms of its specific embodiments, certain modification and equivalents will be apparent to those skilled in art and the intended to be included within the scope of the invention.

All referenced publications, patents and patent documents are intended to be incorporated by reference, as though individually incorporated by reference.

We claim:

1. A process for the preparation of enzalutamide of Formula (I)

the process comprising:
reacting a compound of Formula (VI)

with a compound of Formula (V)

wherein L is Cl, Br, I or a leaving group,
to obtain a compound of Formula (IV)

optionally, purifying the compound of Formula (IV);
reacting the compound of Formula (IV) with a compound of Formula (II)

to obtain the enzalutamide of Formula (I); and
optionally, purifying the enzalutamide of Formula (I) in one or more solvents.

2. The process according to claim 1, wherein the compound of Formula (IV) is reacted with the compound of Formula (II) in presence of a base in one or more solvents.

3. The process according to claim 2, wherein the base comprises of inorganic base or organic base wherein the inorganic base comprises one or more of sodium hydroxide, potassium hydroxide, lithium hydroxide; sodium carbonate, potassium carbonate, sodium bicarbonate, potassium bicarbonate; and ammonia or its aqueous solution; or the organic base comprises one or more of methyl amine, ethyl amine, TEA, TBA, DIPA, DIPEA, pyridine, piperidine, morpholine, DBU, DABCO and DBN.

4. The process according to claim 2, wherein the solvent comprises one or more of esters selected from ethyl acetate, isopropyl acetate, t-butyl acetate, and isobutyl acetate; hydrocarbons selected from toluene, xylene, ethyl benzene, heptane, hexane, and cyclohexane; and chlorinated solvents selected from methylene dichloride, ethylene dichloride, chlorobenzene, chloroform, and carbon tetrachloride.

5. The process according to claim 1, wherein the purification of compound (IV) is performed in one or more solvents comprises of alcohols selected from methanol, ethanol, isopropanol, butanol, t-butanol, and isoamylalcohol; ketones selected from acetone, methyl isobutyl ketone, and methyl ethyl ketone; esters selected from ethyl acetate, isopropyl acetate; t-butyl acetate, and isobutyl acetate; and chlorinated solvents selected from methylene dichloride, ethylene dichloride, and chlorobenzene.

6. The process according to claim 1, wherein enzalutamide of Formula (I) is obtained in crystalline Form-A characterized by x-ray powder diffraction (XRD) having characteristic peaks expressed in degrees 2θ (±0.2° 2θ) at about 13.1°, 13.4°, 14.3°, 16.6°, 21.1°, 22.7° and 24.4°±0.2° 2θ and/or by differential scanning calorimetry (DSC) having onset at about 197±5° C. and an endothermic peak at about 198±5° C.

* * * * *